(12) United States Patent
Palermo (10) Patent No.: US 8,657,821 B2
(45) Date of Patent: Feb. 25, 2014

(54) METHOD AND SYSTEM FOR REVERSIBLY CONTROLLED DRILLING OF LUMINAL OCCLUSIONS

(75) Inventor: Thomas Palermo, San Jose, CA (US)

(73) Assignee: Revascular Therapeutics Inc., Sunnyvale, CA (US)

(*) Notice: Subject to any disclaimer, the term of this patent is extended or adjusted under 35 U.S.C. 154(b) by 1442 days.

(21) Appl. No.: 12/271,712

(22) Filed: Nov. 14, 2008

(65) Prior Publication Data

US 2010/0125276 A1    May 20, 2010

(51) Int. Cl.
*A61B 17/00* (2006.01)

(52) U.S. Cl.
USPC .............. 606/80; 408/1 R; 606/91; 606/159

(58) Field of Classification Search
USPC .................................... 606/80, 159
See application file for complete search history.

(56) References Cited

U.S. PATENT DOCUMENTS

| | | |
|---|---|---|
| 4,068,660 A | 1/1978 | Beck |
| 4,368,730 A | 1/1983 | Sharrock |
| 4,377,169 A | 3/1983 | Banks |
| 4,445,509 A | 5/1984 | Auth |
| 4,471,779 A | 9/1984 | Antoshkiw et al. |
| 4,490,421 A | 12/1984 | Levy |
| 4,516,972 A | 5/1985 | Samson |
| 4,534,363 A | 8/1985 | Gold |
| 4,538,622 A | 9/1985 | Samson et al. |
| 4,545,390 A | 10/1985 | Leary |
| 4,548,206 A | 10/1985 | Osborne |
| 4,554,929 A | 11/1985 | Samson et al. |
| 4,573,470 A | 3/1986 | Samson et al. |
| 4,586,923 A | 5/1986 | Gould et al. |
| 4,601,705 A | 7/1986 | McCoy |
| 4,613,385 A | 9/1986 | Thomas et al. |
| 4,616,653 A | 10/1986 | Samson et al. |
| 4,619,263 A | 10/1986 | Frisbie et al. |
| 4,641,654 A | 2/1987 | Samson et al. |
| 4,646,719 A | 3/1987 | Neuman et al. |
| 4,646,736 A | 3/1987 | Auth |
| 4,646,742 A | 3/1987 | Packard et al. |
| 4,676,249 A | 6/1987 | Arenas et al. |
| 4,708,717 A | 11/1987 | Deane et al. |
| 4,708,718 A | 11/1987 | Daniels |
| 4,715,378 A | 12/1987 | Pope, Jr. et al. |
| 4,717,387 A | 1/1988 | Inoue et al. |
| 4,719,924 A | 1/1988 | Crittenden et al. |
| 4,721,117 A | 1/1988 | Mar et al. |

(Continued)

OTHER PUBLICATIONS

International Search Report and Written Opinion of PCT Application No. PCT/US2009/063985, mailed Jan. 7, 2010, 8 pages total.

(Continued)

*Primary Examiner* — David H Willse
*Assistant Examiner* — Tiffany Shipmon
(74) *Attorney, Agent, or Firm* — Seager, Tufte & Wickhem, LLC (57) ABSTRACT

A luminal drilling system includes a drilling device and a control unit. The drilling device includes an elongate member having a drive shaft with a drill tip. The control unit includes a motor connectable to the drive shaft and control circuitry which rotationally oscillates the drive shaft with the direction of rotation automatically reversing whenever the load on the motor and/or drive shaft exceeds a threshold value.

18 Claims, 10 Drawing Sheets

(56) References Cited

U.S. PATENT DOCUMENTS

| | | |
|---|---|---|
| 4,723,936 A | 2/1988 | Buchbinder et al. |
| 4,739,768 A | 4/1988 | Engelson |
| 4,763,647 A | 8/1988 | Gambale |
| 4,767,400 A | 8/1988 | Miller et al. |
| 4,779,628 A | 10/1988 | Machek |
| 4,798,598 A | 1/1989 | Bonello et al. |
| 4,832,047 A | 5/1989 | Sepetka et al. |
| 4,846,186 A | 7/1989 | Box et al. |
| 4,899,787 A | 2/1990 | Ouchi et al. |
| 4,906,241 A | 3/1990 | Noddin et al. |
| 4,923,462 A | 5/1990 | Stevens |
| 4,925,445 A | 5/1990 | Sakamoto et al. |
| 4,926,858 A | 5/1990 | Gifford, III et al. |
| 4,940,062 A | 7/1990 | Hampton et al. |
| 4,946,466 A | 8/1990 | Pinchuk et al. |
| 4,953,553 A | 9/1990 | Tremulis |
| 4,979,939 A | 12/1990 | Shiber |
| 4,990,134 A | 2/1991 | Auth |
| 5,021,044 A | 6/1991 | Sharkawy |
| 5,030,204 A | 7/1991 | Badger et al. |
| 5,041,082 A | 8/1991 | Shiber |
| 5,041,085 A | 8/1991 | Osborne et al. |
| 5,059,851 A | 10/1991 | Corl et al. |
| 5,060,660 A | 10/1991 | Gambale et al. |
| 5,067,489 A | 11/1991 | Lind |
| 5,107,582 A | 4/1992 | Kessler |
| 5,107,852 A | 4/1992 | Davidson et al. |
| 5,115,814 A | 5/1992 | Griffith et al. |
| 5,116,350 A | 5/1992 | Stevens |
| 5,144,959 A | 9/1992 | Gambale et al. |
| 5,156,157 A | 10/1992 | Valenta, Jr. et al. |
| 5,165,421 A | 11/1992 | Fleischhacker et al. |
| 5,176,661 A | 1/1993 | Evard et al. |
| 5,178,158 A | 1/1993 | de Toledo |
| 5,184,627 A | 2/1993 | de Toledo |
| 5,195,954 A | 3/1993 | Schnepp-Pesch et al. |
| 5,195,971 A | 3/1993 | Sirhan |
| 5,209,727 A | 5/1993 | Radisch, Jr. et al. |
| 5,211,636 A | 5/1993 | Mische |
| 5,217,482 A | 6/1993 | Keith |
| 5,250,034 A | 10/1993 | Appling et al. |
| 5,263,959 A | 11/1993 | Fischell |
| 5,267,979 A | 12/1993 | Appling et al. |
| RE34,556 E | 3/1994 | Sjostrom et al. |
| 5,306,252 A | 4/1994 | Yutori et al. |
| 5,314,407 A | 5/1994 | Auth et al. |
| 5,314,438 A | 5/1994 | Shturman |
| RE34,695 E | 8/1994 | Mar et al. |
| 5,345,945 A | 9/1994 | Hodgson et al. |
| 5,346,473 A | 9/1994 | Bowman |
| 5,348,017 A | 9/1994 | Thornton et al. |
| 5,358,485 A | 10/1994 | Vance et al. |
| 5,366,464 A | 11/1994 | Belknap |
| 5,368,035 A | 11/1994 | Hamm et al. |
| 5,372,602 A | 12/1994 | Burke |
| 5,377,690 A | 1/1995 | Berthiaume |
| 5,378,234 A | 1/1995 | Hammerslag et al. |
| 5,391,147 A | 2/1995 | Imran et al. |
| 5,462,523 A | 10/1995 | Samson et al. |
| 5,476,473 A | 12/1995 | Heckele |
| 5,484,407 A | 1/1996 | Osypka |
| 5,507,738 A | 4/1996 | Ciervo |
| 5,510,070 A | 4/1996 | Krause et al. |
| 5,527,298 A | 6/1996 | Vance et al. |
| 5,527,326 A | 6/1996 | Hermann et al. |
| 5,531,677 A | 7/1996 | Lundquist et al. |
| 5,540,707 A | 7/1996 | Ressemann et al. |
| 5,563,482 A | 10/1996 | Shaw et al. |
| 5,569,197 A | 10/1996 | Helmus et al. |
| 5,571,085 A | 11/1996 | Accisano, III |
| 5,591,142 A | 1/1997 | Van Erp |
| 5,606,981 A | 3/1997 | Tartacower et al. |
| 5,611,777 A | 3/1997 | Bowden et al. |
| 5,632,755 A | 5/1997 | Nordgren et al. |
| 5,651,785 A | 7/1997 | Abela et al. |
| 5,657,000 A | 8/1997 | Ellingboe |
| 5,662,671 A | 9/1997 | Barbut et al. |
| 5,663,886 A | 9/1997 | Lueck |
| 5,672,945 A | 9/1997 | Krause |
| 5,681,336 A | 10/1997 | Clement et al. |
| 5,689,194 A | 11/1997 | Richards et al. |
| 5,766,016 A | 6/1998 | Sinclair et al. |
| 5,772,609 A | 6/1998 | Nguyen et al. |
| 5,776,114 A | 7/1998 | Frantzer |
| 5,820,591 A | 10/1998 | Thompson et al. |
| 5,830,219 A | 11/1998 | Bird et al. |
| 5,843,103 A | 12/1998 | Wulfman |
| 5,848,986 A | 12/1998 | Lundquist et al. |
| 5,860,938 A | 1/1999 | LaFontaine et al. |
| 5,865,800 A | 2/1999 | Mirarchi et al. |
| 5,868,685 A | 2/1999 | Powell et al. |
| 5,897,567 A | 4/1999 | Ressemann et al. |
| 5,908,395 A | 6/1999 | Stalker et al. |
| 5,922,003 A | 7/1999 | Anctil et al. |
| 6,001,112 A | 12/1999 | Taylor |
| 6,022,336 A | 2/2000 | Zadno-Azizi et al. |
| 6,050,972 A | 4/2000 | Zadno-Azizi et al. |
| 6,056,743 A | 5/2000 | Ellis et al. |
| 6,059,767 A | 5/2000 | Noriega |
| 6,066,149 A | 5/2000 | Samson et al. |
| 6,068,623 A | 5/2000 | Zadno-Azizi et al. |
| 6,093,157 A | 7/2000 | Chandrasekaran |
| 6,120,515 A | 9/2000 | Rogers et al. |
| 6,152,909 A | 11/2000 | Bagaoisan et al. |
| 6,156,046 A | 12/2000 | Passafaro |
| 6,179,851 B1 | 1/2001 | Barbut et al. |
| 6,217,567 B1 | 4/2001 | Zadno-Azizi et al. |
| 6,234,971 B1 | 5/2001 | Jang |
| 6,258,052 B1 | 7/2001 | Milo |
| 6,299,622 B1 | 10/2001 | Snow |
| 6,312,438 B1 | 11/2001 | Adams |
| 6,355,014 B1 | 3/2002 | Zadno-Azizi et al. |
| 6,375,628 B1 | 4/2002 | Zadno-Azizi et al. |
| 6,387,109 B1 | 5/2002 | Davison et al. |
| 6,482,217 B1 | 11/2002 | Pintor et al. |
| 6,482,221 B1 | 11/2002 | Hebert et al. |
| 6,500,130 B2 | 12/2002 | Gordon et al. |
| 6,533,749 B1 | 3/2003 | Mitusina et al. |
| 6,585,717 B1 | 7/2003 | Wittenberger et al. |
| 6,602,264 B1 | 8/2003 | McGurckin |
| 6,652,508 B2 | 11/2003 | Griffin et al. |
| 6,743,208 B1 | 6/2004 | Coyle |
| 6,746,422 B1 | 6/2004 | Noriega et al. |
| 6,824,550 B1 | 11/2004 | Noriega et al. |
| 7,107,096 B2 | 9/2006 | Fischell et al. |
| 7,381,198 B2 | 6/2008 | Noriega et al. |
| 7,479,147 B2 | 1/2009 | Honeycutt et al. |
| 7,628,763 B2 | 12/2009 | Noriega et al. |
| 2001/0004700 A1* | 6/2001 | Honeycutt et al. ............ 606/159 |
| 2003/0015977 A1 | 1/2003 | Lee et al. |
| 2005/0020974 A1 | 1/2005 | Noriega et al. |
| 2005/0113853 A1 | 5/2005 | Noriega et al. |
| 2005/0119615 A1 | 6/2005 | Noriega et al. |
| 2005/0228418 A1 | 10/2005 | Noriega et al. |
| 2006/0074442 A1 | 4/2006 | Noriega et al. |
| 2006/0106363 A1* | 5/2006 | Aravena et al. ............... 604/506 |
| 2006/0259052 A1 | 11/2006 | Pintor |
| 2007/0175949 A1 | 8/2007 | Shelton |
| 2007/0225615 A1 | 9/2007 | Chechelski et al. |
| 2007/0239140 A1 | 10/2007 | Chechelski et al. |
| 2008/0140101 A1* | 6/2008 | Carley et al. .................. 606/159 |
| 2008/0221601 A1 | 9/2008 | Huynh et al. |
| 2009/0062804 A1* | 3/2009 | Runquist et al. ................ 606/80 |

OTHER PUBLICATIONS

"Low Cost Monolithic Voltage-to-Frequency Converter," (Product AD654 Description); Analog Devices, Dec. 1999, pp. 1-11.

* cited by examiner

| Fig. 6A | Fig. 6B |

METHOD AND SYSTEM FOR REVERSIBLY CONTROLLED DRILLING OF LUMINAL OCCLUSIONS

CROSS-REFERENCES TO RELATED APPLICATIONS

The present application is related to but does not claim priority from application Ser. No. 11/388,251, filed on Mar. 22, 2006, and application Ser. No. 11/636,388, filed on Dec. 7, 2006, the full disclosures of which are incorporated herein by reference.

BACKGROUND OF THE INVENTION

1. Field of the Invention

The present invention relates generally to medical methods and systems. More particularly, the present invention relates to a method and driver for the controlled, reversible drilling of an occlusion in a body lumen, such as a calcific occlusion in a blood vessel.

Cardiovascular disease frequently arises from the accumulation of atheromatous material on the inner walls of vascular lumens, particularly arterial lumens of the coronary and other vasculature, resulting in a condition known as atherosclerosis. Atheromatous and other vascular deposits restrict blood flow and can cause ischemia which, in acute cases, can result in myocardial infarction or a heart attack. Atheromatous deposits can have widely varying properties, with some deposits being relatively soft and others being fibrous and/or calcified. In the latter case, the deposits are frequently referred to as plaque. Atherosclerosis occurs naturally as a result of aging, but may also be aggravated by factors such as diet, hypertension, heredity, vascular injury, and the like.

Atherosclerosis can be treated in a variety of ways, including drugs, bypass surgery, and a variety of catheter-based approaches which rely on intravascular widening or removal of the atheromatous or other material occluding the blood vessel. Particular catheter-based interventions include angioplasty, atherectomy, laser ablation, stenting, and the like. For the most part, the catheters used for these interventions must be introduced over a guidewire, and the guidewire must be placed across the lesion prior to catheter placement. Initial guidewire placement, however, can be difficult or impossible in tortuous regions of the vasculature. Moreover, crossing the occlusion with a guidewire is even more difficult if the lesion is total or near total, i.e. the lesion occludes the blood vessel lumen to such an extent that the lesion blocks advancement of the guidewire. Crossing the lesion is further exacerbated if the plaque is hardened or "calcific."

To overcome this difficulty, forward-cutting atherectomy catheters have been proposed. Such catheters usually can have a forwardly disposed blade (U.S. Pat. No. 4,926,858) or rotating burr (U.S. Pat. No. 4,445,509). While effective in some cases, these catheter systems, even when being advanced through the body lumen with a separate guidewire, have great difficulty in traversing through the small and tortuous body lumens of the patients and reaching the target site.

As an improvement over forward cutting atherectomy catheters, the use of small guidewire-sized devices for crossing lesions has been proposed. Such devices can include a hypotube body or other relatively rigid shaft having a more flexible distal portion which is suitable for passing through small and tortuous regions of the vasculature and other body lumens. A very small drive shaft having a cutting element at its distal end is disposed in a lumen of the tubular body and extends from a distal end thereof. By rapidly rotating or rotationally oscillating the drive shaft, the cutting tip can penetrate even hardened, calcific occlusions. Such devices are described in detail in commonly owned U.S. Pat. Nos. 6,059,767 and 6,824,550, as well as co-pending application Ser. Nos. 10/950,161; 10/999,457; 11/146,483; 11/236,703; and 11/567,884, the full disclosures of which are incorporated herein by reference.

While very effective for crossing hardened lesions in the coronary and other vasculature, the rotating cutting tips can experience excessive friction and constriction when being advanced into the occlusion. The friction can come from the guidewire being advanced into the occlusion with excessive force, thus advancing the rotating tip too rapidly into the occlusion. Additionally, rotation of the tip can be limited by loose tissue wrapping around the tip. In either case, the constriction of the tip rotation can result in excessive torque being experienced by the drive shaft and motor. At a minimum, the excessive torque can hinder the performance of the guidewire and make advancement more difficult. More problematically, such excessive torque can damage the motor and/or fracture the guidewire shaft.

One solution to the problem of excessive torque in such cutting guidewires has been to employ rotational oscillation rather than unidirectional rotation of the cutting tip. Using a relatively high rotational speed, such as 12,000 rpm, and changing the rotational direction every 0.7 seconds, has been found to reduce but not eliminate the problems associated with constriction of the cutting tip as it is advanced through calcific and other lesions. Additionally, as described in commonly owned, co-pending application Ser. Nos. 11/388,251 and 11/636,388, the full disclosures of which are incorporated herein by reference, systems for rotationally oscillating drive shafts in cutting guidewires can be modified to monitor the load on the drive shaft and/or drive motor and to provide visual and/or audible feedback to the treating physician. The physician is alerted when the torque on the system approaches an unacceptable level so that the physician may pull back on the guidewire to relieve the constricting forces. While very effective and a significant advancement, changing rotational direction at a fixed interval does not optimize cutting efficiency.

For these reasons, it would be desirable to provide improved methods and systems for advancing cutting guidewires and other similar catheter systems through a body lumen. In particular, it would be desirable to provide methods and systems where control of a cutting tip of such guidewires and catheters is automatically adjusted in response to variations in the constrictive forces on the cutting tip as the guidewire or other catheter is advanced through occlusions in a body lumen. It would be particularly desirable if such automatic control of the cutting guidewire could be combined with the visual and audible feedback systems described above. At least some of these objectives will be met by the inventions described hereinbelow.

2. Description of Background Art

Exemplary cutting guidewire devices and control systems for providing visual and/or audible feedback on the level of torque experienced by the motors and drive shafts of such systems are described in the commonly owned patents and co-pending applications referenced above.

BRIEF SUMMARY OF THE INVENTION

The present invention provides systems and methods for automatic controlling a cutting tip during crossing of stenoses, partial occlusions, total occlusions, or chronic total occlusions in a patient's body, such as in a blood vessel or other body lumen. The devices for penetrating occlusive material and passing through occlusions, stenosis, thrombus, plaque, calcified material, and other material in a neuro, coronary, and peripheral body lumens generally include a hollow, elongate member, typically a tubular shaft, that is advanced through a blood vessel lumen and positioned adjacent the occlusion or stenosis. A drilling assembly, typically including a drill tip or other cutting head, is positioned at or near a distal tip of the hollow member to penetrate or create an opening in the occlusion. The plaque drilling assembly generally comprises a drive shaft having a distal tip that is rotated and optionally rotationally oscillated (e.g., rotated in one direction for a period of time, then rotated in the reverse direction for a period of time if the drill tip or other cutting head encounters a load at or above a predetermined threshold), where the distal drill tip emerges distally from an axial lumen of the hollow member. Once the hollow, elongate member has reached the lesion, the hollow member with the exposed rotationally oscillating drill tip may be advanced into the lesion.

In a first aspect of the present invention, methods for advancing the elongate member across the occlusion comprise advancing a distal end of the elongate member into the occlusion while rotating a drive shaft having a drill tip extending distally from the distal end of the elongate member. The drive shaft is rotated as the elongate member is advanced into the occlusion. While the elongate member is being advanced, a rotational load on the drive shaft is measured. The rotational load may be measured in a variety of ways, but typically will be measured either by monitoring the current load on a motor which drives the drive shaft or monitoring the rotational speed of the drive shaft. When monitoring the current load, an increase in the drive current indicates that the load on the drive shaft is increasing. When monitoring the rotational speed, a decrease in speed indicates that the rotational load on the drive shaft is increasing. In either case, when the measured load on the drive shaft meets or exceeds a preselected threshold value, the rotational direction of the drive shaft is reversed. After the direction is reversed, the load on the drive shaft will be expected to drop significantly, but the load will continue to be monitored and when it again exceeds the preselected threshold value, the direction will again be reversed.

Usually, the drive shaft and drill tip are rotated up to maximum speed in the range from 1,000 rpm to 100,000 rpm, typically from 5,000 rpm to 20,000 rpm. It will be appreciated, of course, that every time the direction of rotation is reversed, the instantaneous rotational speed will be zero. Usually, the maximum rotational speed will then be achieved in a time from about 0.001 seconds to 1 seconds after the direction has been reversed.

The threshold value of load at which the direction of drive shaft rotation is reversed will be selected to limit the maximum torque experienced by the drill tip, drive shaft, and motor to a level which is safe both for the patient and for the luminal drilling system. In one example, threshold value can be set to reverse direction when loose tissue wrapping occurs allowing the user to continue advancing or pull back the luminal drilling system with minimal force. If the rotational direction is not reversed, excessive loose tissue wrapping may cause the rotating tip to become trapped and make it difficult for the user to pull back or advance. In another example, the threshold value can be set to reverse directions at a torque value allowing for an acceptable fatigue life of the driveshaft. If the rotational direction is not reversed the torque would reach a level causing fracture and/or fatigue. In a third example, the threshold value can be set to allow for rotation in one direction when the user is advancing the elongate member into the occlusion with an acceptable axial push force, but the threshold will be exceeded and the controller will reverse direction of the motor, typically when the user is applying too large of an axial push force to the elongate member. This will allow for maximum cutting efficiency in normal use, while controlling the maximum torque allowed if the user advances with too much axial push force as a safety feature. When the rotational load is measured by monitoring current on the motor which rotates the drive shaft, the threshold value will be based on a percentage increase from the current value when the driveshaft is rotating with no torque applied to the drill tip. For example, if the load value was 0.10 Amps when the driveshaft is rotating with no torque on the drill tip, the threshold may be set to 0.50 Amps which is a 500% larger value. This percentage increase will vary depending on the selected maximum torque limit.

In the case where the rotational load is measured by monitoring the rotational speed of the drive shaft, the threshold value will typically be set to reverse direction when the rotational speed decreases by from 25% to 100%, more preferably when the rotational speed decreases by from 50% to 75%. Using an encoder, a specific rpm (absolute value) would be set to trigger a reverse of directions. For example, if the motor rotated at 12,000 rpm, the threshold could be set at 5,000 rpm. While speed measurement is feasible, current measurement is the preferred present approach.

In some methods, it will be desirable to allow the threshold load value to be adjusted within certain ranges before and/or during a procedure. Thus, the physician can adjust the system for differences in the occlusive material which is being encountered in the procedure.

In addition to the automatic control of the rotational direction of the drill tip, the methods of the present invention may further comprise producing an audible or visual output which is representative of the measured amount of load on the motor or drive shaft. Still further, the systems may produce an audible and/or visual output whenever the threshold load value is met or exceeded and the rotational direction is reversed.

In a second aspect of the present invention, a luminal drilling system comprises a drilling device including an elongate member and a drive shaft extending through said member. The drive shaft has a drill tip at its distal end which emerges distally from a distal end of the elongate member. A motor is connectable to a proximal portion of the drive shaft to rotationally drive the drive shaft, and a load sensor is coupled to the motor and/or to the drive shaft for monitoring load on the drive shaft and the drill tip. The load sensor produces an output signal which is representative of the rotational load as the tip is rotated and advanced through occlusive material in a body lumen, such as calcific plaque in a blood vessel. The system further includes motor control circuitry which reverses the direction of rotation of the motor when the sensed rotational load meets or exceeds a threshold value, where the threshold value is typically selected to assure the safety of the patient and the system, as discussed above in connection with the methods of the present invention.

The elongate member of the drilling device typically comprises a tube, such as a hypotube, having a diameter in the range from 0.008 in. to 0.04 in. typically from 0.009 in. to 0.035 in. In some embodiments, the motor will be fixedly connected to the drive shaft, while in other embodiments the motor may be detached from the drive shaft. In most embodiments, the drill tip will have a symmetric or other design which allows the drill tip to penetrate equally well in both rotational directions.

The motor of the luminal drilling system will usually be incorporated in an enclosure. The control circuitry may be contained in the same enclosure as the motor or may be in a separate enclosure connected by a cord. The enclosure will be coupled to the elongate member in the shaft of the drilling device, where the motor in particular is coupled to the drive shaft to rotate the drive shaft relative to the elongate member. The motor will provide for reversible rotation of the drive shaft and will be controllable to rotate at a maximum speed in the range from 1,000 rpm to 100,000 rpm, typically from 5,000 rpm to 20,000 rpm, in both directions. The load sensor will usually also be incorporated into the enclosure together with the control circuitry. The load sensor may be adapted to measure current consumption by the motor, where an increase in current consumption indicates an increase in load. Alternatively, the load sensor may be adapted to measure the rotational speed of the motor or the drive shaft, where a decrease in rotational speed indicates an increase in load. Rotational speed may be measured, for example, using an encoder on the drive shaft and an optical system for measuring rotational speed and direction. Other conventional systems for measuring motor speed and/or shaft rotational speed could also be utilized.

The luminal drilling systems of the present invention may further comprise circuitry which produces a visual and/or audible output in response to the output signal of the load sensor. For example, the visual and/or audible output may comprise a first output level where the load is below the threshold value and a second output level when the load is at or above the threshold level, where the second output level would then indicate that the motor direction is changing. Alternatively, the visual and/or output may comprise additional output levels, for example a first output level when there is no or minimal load on the motor and/or shaft, a second output level when there is a load on the motor and/or shaft below the threshold value, and a third output level when the load is at or above the threshold value to indicate that the motor direction is changing.

In a third aspect of the present invention, a rotational driver for connection to a luminal drilling device is provided. The luminal drilling device will typically have the characteristics described above in connection with the luminal drilling system. The rotational driver will include a motor adapted to rotationally drive the drive shaft, a load sensor coupled to the motor or to the drive shaft, and motor control circuitry which reverses the direction of rotation of the motor when the sensed rotational load exceeds a threshold value. Other aspects of the motor, load sensor, and motor control circuitry have been described above with respect to the luminal drilling system.

BRIEF DESCRIPTION OF THE DRAWINGS

The following drawings should be read with reference to the detailed description. Like numbers in different drawings refer to like elements. The drawings, which are not necessarily to scale, illustratively depict embodiments of the present invention and are not intended to limit the scope of the invention.

DETAILED DESCRIPTION OF THE INVENTION

Figure 1:
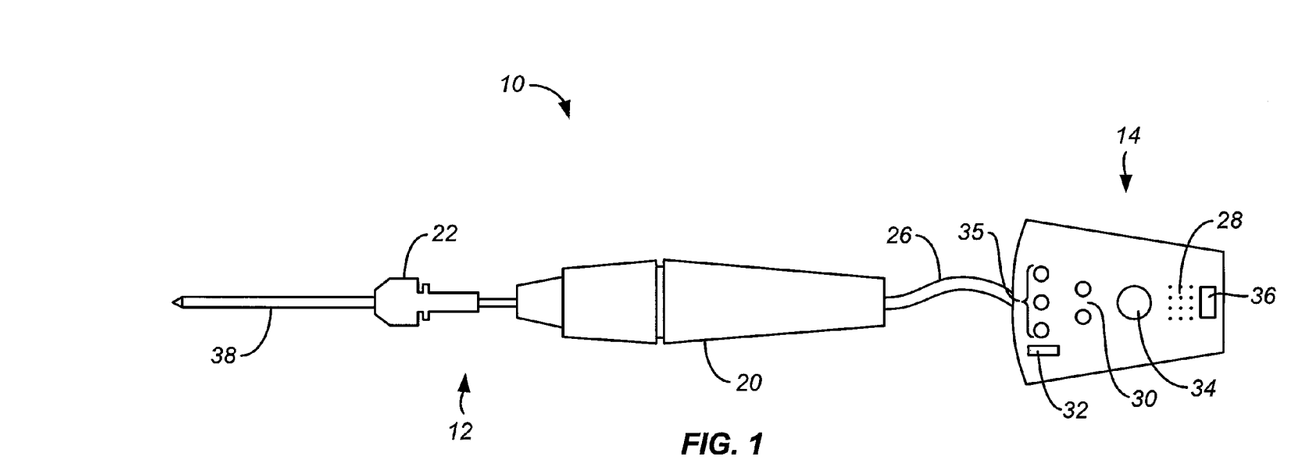
FIG. 1 illustrates an exemplary luminal drilling system constructed in accordance with the principles of the present invention.
Figure 2:
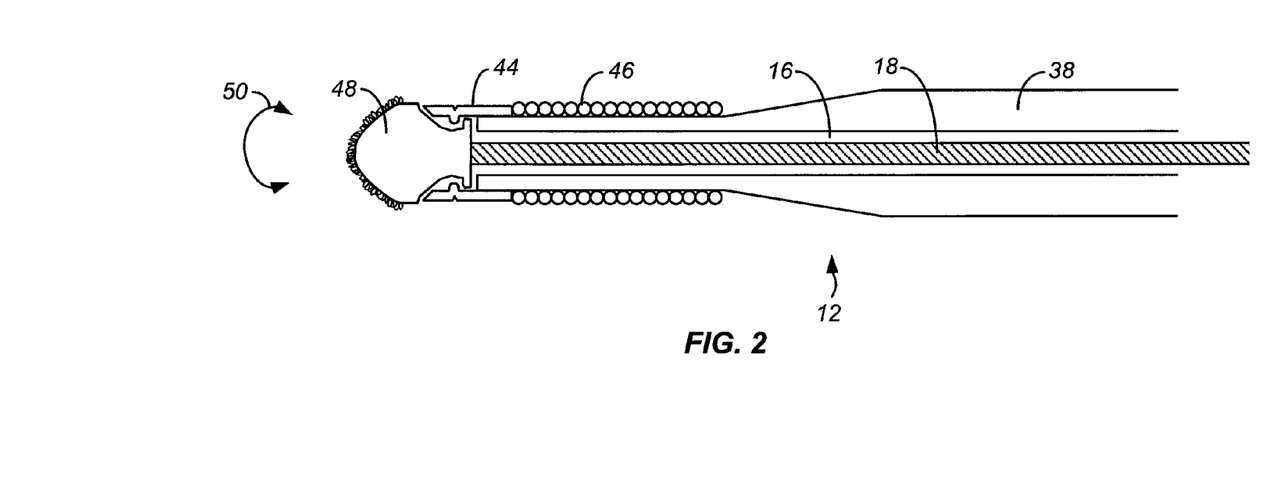
FIG. 2 illustrates an exploded view of a distal end portion of a drilling device of the system of FIG. 1 comprising a drive shaft disposed within a hollow, shapeable member.

Referring now to FIG. 1, an exemplary luminal drilling system 10 constructed in accordance with the principles of the present invention is illustrated. The system 10 includes a drilling device 12 configured to cross an occlusion and a control unit 14. The drilling device 12 includes an elongate flexible member 38 having an axial lumen 16 and a drive shaft 18 extending through the axial lumen 16, as best shown in FIG. 2. An adjustable torquer 22 is placed over the elongate flexible member 38. The adjustable torquer 22 may be axially moved along the elongate flexible member 38 and locked down anywhere along the length of the elongate flexible member 38. A motor housing 20 is coupled to a proximal end of the device 12. The control unit 14 is coupled to the motor housing 20 via wire leads or cables 26. The motor housing 20 includes a motor 56 (FIG. 3) to rotationally oscillate the drive member. The control unit 14 includes control circuitry for reversing the direction of rotation, as described in more detail below. In addition to providing audible and/or visual feedback on system load, the control unit may optionally include a speaker 28, volume control buttons 30 which may adjust audio amplification, a main on/off power supply switch or pull out tab 32, a motor activation switch 34, a display comprising a linear array of light emitting diodes (LED) 35, and a timer liquid crystal display (LCD) 36. The control unit will usually be relatively small, having a length in a range from about 5 cm to about 25 cm, a width in a range from about 2 cm to about 12 cm, and a depth in a range from about 1 cm to about 8 cm. In some instances, the control unit could be dimensioned to be hand held. It will be appreciated that the above depictions are for illustrative purposes only and do not necessarily reflect the actual shape, size, or dimensions of the controller system 10. This applies to all depictions hereinafter.

Referring now to FIG. 2, the drilling device 12 of the present invention will usually have sufficient steerability, shapeability, flexibility, pushability, and torqueability to be advanced through the tortuous blood vessel without the use of a separate guidewire or other guiding element. In some instances, however, the drilling devices will be rigid and configured for surgical applications and/or configured for delivering over a guidewire or through a guide catheter. Additionally, the device 12 may be sized to fit within an axial lumen of a distal support or access catheter system (not shown), which is described in more detail in U.S. patent application Ser. No. 10/864,075, filed Jun. 8, 2004, assigned to the assignee of the present application and incorporated herein by reference. The distal support catheter system can be delivered either concurrently or sequentially with the advancement of the device 12 to the target site. The position of the catheter system can be maintained and stabilized while the device 12 is advanced.

The drilling device 12, which is generally but not identically described in co-pending U.S. patent application Ser. No. 11/236,703, and the other applications cross-referenced above, comprises an elongate hollow shapeable member 38 having a proximal portion, a shapeable distal portion, and a flexible intermediate portion along a length therebetween. In one embodiment, the distal portion of the elongate member 38 may have a fixed, preset deflection. The elongate hollow member 38 movably receives the drive shaft 18 within its axial lumen 16 and is coupled to the motor housing 20 on the proximal portion. That is, the drive shaft 18 is received within axial lumen 16 and is movable therein. The elongate hollow member 38 may be composed of a unitary structure, such as a single hypotube, having one or more tapered sections. The elongate hollow member 38 may be formed from a variety of materials, including nitinol, stainless steel, polymer, carbon, or other metal or composite materials. The elongate member 38 may have an outer diameter in a range from about 0.008 inch to about 0.040 inch, an inner diameter in a range from about 0.005 inch to about 0.036 inch, and a working length in a range from about 125 cm to about 190 cm, as for example in FIG. 1 the length is illustrated as approximately 165 cm.

Referring again to FIG. 2, an exploded view of the distal end portion of the device 12 shows tip housing 44 attached to the hollow member 38. The tip housing 44 contains a proximal portion of the distal tip 48. The tip housing 44 may be crimped to prevent the distal tip 48 from detaching if a fracture occurs in the drive shaft 18. The tip housing 44 may be plated with a radiopaque material such as gold. A radiopaque coil, such as platinum-tungsten, may be attached to the hollow member 38 just proximal to the tip housing 44 to increase the length of the radiopaque section. The hollow member 38 may be shaped proximal to the tip housing 44. Shaping may be performed through plastic deformation or heat setting. Drive shaft 18 is disposed within the axial lumen 16 of the elongate hollow member 38. The drive shaft 18 is rotatably disposed at the distal end of the elongate hollow member 38. A distal tip 48 of the drive shaft 18 extends through a distal opening of the lumen 16 and emerges distally from the distal end of the hollow member 38. The distal tip 48 may be covered with an abrasive material, for example diamond like coating (DLC). Upon activation, the distal tip 48 of the drive shaft 18 creates a passageway or enlarges a passageway through the occlusion or stenosis within the vessel lumen. Generally, the distal tip 48 of the drive shaft 18 creates a path at least as large as a perimeter of a distal end of the hollow member 38. However, it will be appreciated that the path can also have the same perimeter or smaller perimeter than the distal end of the hollow member 38.

The drive shaft 18 in this embodiment is rotationally reversed, as depicted by arrow 50, when the motor and/or drill tip encounters an excessive load. The rotationally reversing operating mode 50 is of particular benefit as it inhibits excessive tissue from wrapping around the distal tip 48 of the drive shaft 18. This reversing rotation (i.e., rotation in one direction until an excess load is encountered followed by rotation in the reverse direction until an excess load is encountered) also enhances penetration through, in, and/or out of the occlusive or stenotic material. The direction of rotation of the drive shaft 18 will be automatically reversed in response to an increase in load on the motor and/or drive shaft. Generally, rotation of the drive shaft 18 is effected by a drive motor within the motor housing 20, which is described in more detail below. Optionally, the physician may also manually rotate the drive shaft 18.

The drive shaft 18 may be formed from a variety of materials, including nitinol (nickel-titanium alloy), stainless steel, platinum iridium, and like materials and will usually have a diameter in a range from about 0.003 inch to about 0.035 inch and a working length in a range from about 125 cm to about 190 cm. The drive shaft distal tip 48 (the drill tip) will preferably have an outer perimeter which is equal to or larger than a distal diameter of the hollow member 38 so as to create a path at least as large as a perimeter of the distal end of the member 38. The distal tip 48 will usually have a symmetric design so that it penetrates equally well in both rotational directions. The diameter of the drive shaft 18 will depend on the dimension of the inner lumen 16 of the hollow member 38.

As mentioned above, for vascular use, the drilling device 12 of the present invention will usually have steerability, shapeability, flexibility, pushability, and torqueability which allow it to be positioned through the tortuous blood vessel. Once properly positioned adjacent the occlusion or stenosis, the distal tip 48 of the drive shaft 18 is rotated and advanced into the occlusion or stenosis in the vessel lumen to create a path in the occlusion or stenosis.

Figure 3:
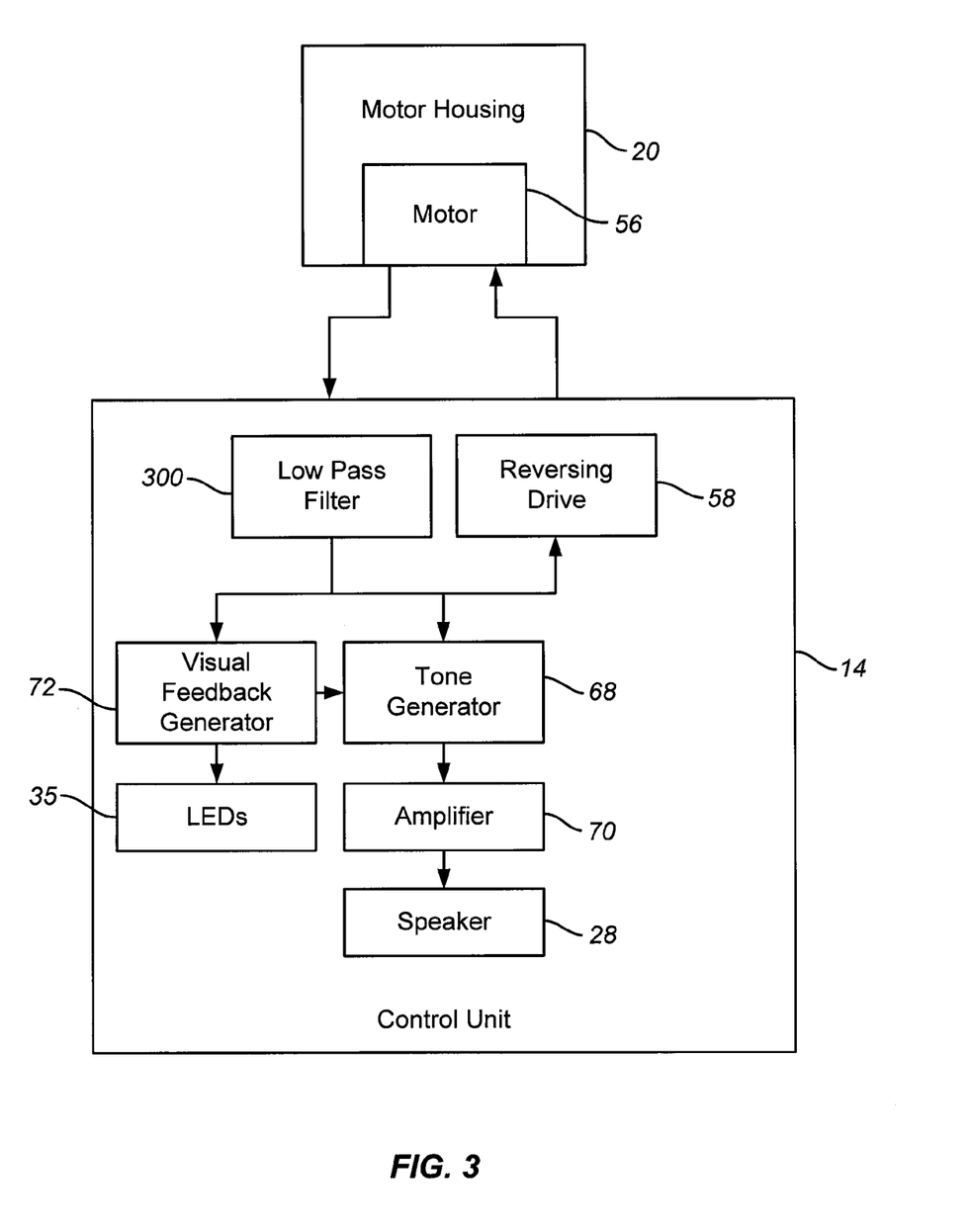
FIG. 3 is a simplified block diagram illustrating the controller system of the present invention.

Referring now to FIG. 3, a simplified block diagram of the controller system 10 of the present invention is illustrated. The control unit 14 may include a low pass filter 300 which removes noise from the motor current signal received from motor 56 and may also provide amplification of the signal. The control unit 14 may also include a V to F generator 68 which produces a variable sound in response to a load measurement (e.g., resistance encountered) on the drive shaft 18, particularly during advancement of the distal tip 48 in the occluded vessel lumen. Generator 68 may be a microprocessor, one or more discrete logic blocks or the like. The signal from the tone generator 68 is then ran through an amplifier 70 to a speaker 28. The load or resistance encountered may be measured by a change in current drawn by the motor 56 which drives the shaft 18, which may be measured by a change in voltage across a feedback resistor. The motor 56 preferably resides within the motor housing 20 and is mechanically attachable to a proximal end of the drive shaft 18 to move (e.g., oscillate, axially translate, reciprocate, rotate, vibrate) the drive shaft 18 and distal tip 48. Typically, the drive motor 56 is electrically coupled to the control unit via the wire leads or cables 26 (FIG. 1). The voltage signal from motor 56 may be directly input into visual feedback generator 72 through filter 300 such that the generator 72 independently provides an appropriate signal to LED display 35 based on the measured voltage across the feedback resistor of the motor. Alternatively, the frequency data generated by V to F generator 68 may be input into generator 72, which may then provide an appropriate signal to LED display 35 based on the frequency data.

The electronic circuitry in the control unit 14, as for example the oscillation system 58, controls The electronic circuitry in the control unit 14, as for example the reversing drive 58, controls reversing of the motor 56 direction. This output mode may be provided by activation of the motor activation switch 34. The accumulated activation time may be constantly displayed on the LCD display 36 on the control unit 14.

Figure 4:
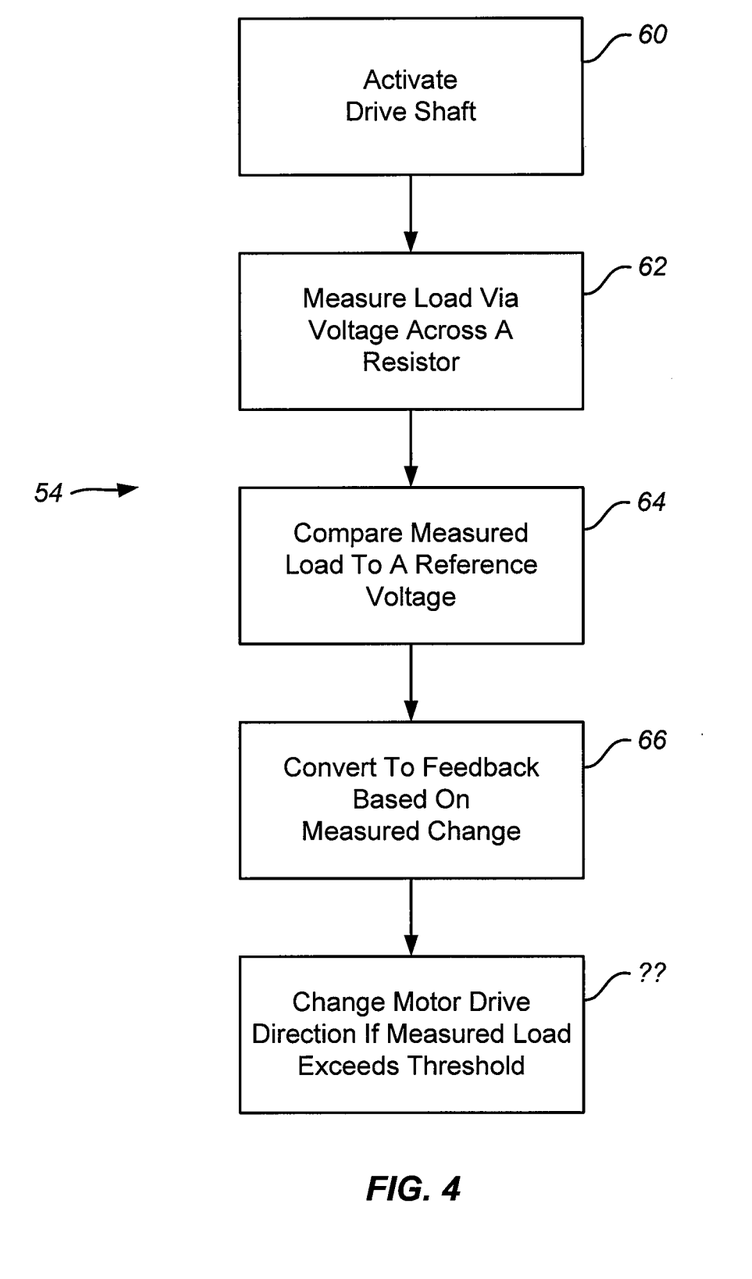
FIG. 4 is a simplified flow diagram illustrating a method for providing control feedback during crossing of an occlusion or stenosis within a vessel lumen in accordance with the principles of the present invention.

Referring now to FIG. 4, the processor 54 in the control unit 14 further measures loads. Measuring a load comprises measuring a change in current drawn by the motor 56 which drives the shaft 18. Typically, the load on the drive motor 56 varies according to the resistance encountered by the drive shaft 18, as for example hard or soft stenosis in the vessel lumen. The load on the motor 56 may be measured through the detection of voltage across a known resistor, as depicted by block 62, which is directly proportional to the current flowing through the resistor. For example, two 1 ohm resistors may be provided for an oscillatory drive shaft 18, one resistor for each direction of the oscillatory drive motor 56. The amperage related voltage is then compared to a reference voltage, as for example 0.53 volts, as depicted by block 64.

As depicted by block 66, the control signal is then produced by converting the change in current (i.e., the difference between the measured load and the reference voltage) to a frequency for sound via a voltage to frequency generator 68 (FIG. 3) and/or a visual display via visual feedback generator 72 (FIG. 3). Use of the control signal for providing visual and/or audible feedback to the physician is described in detail in co-pending application Ser. Nos. 11/388,251 and 11/636,338, which have been previously incorporated herein by reference. As depicted in FIG. 3, the motor drive will change directions if the measured load meets or exceeds a threshold. The following discussion will be directed specifically at the circuitry used for implementing the automatic motor control which reverses the direction of the motor when the control signal indicates that a threshold load value on the motor and/or drive shaft has been exceeded.

Figures 5, 5A:
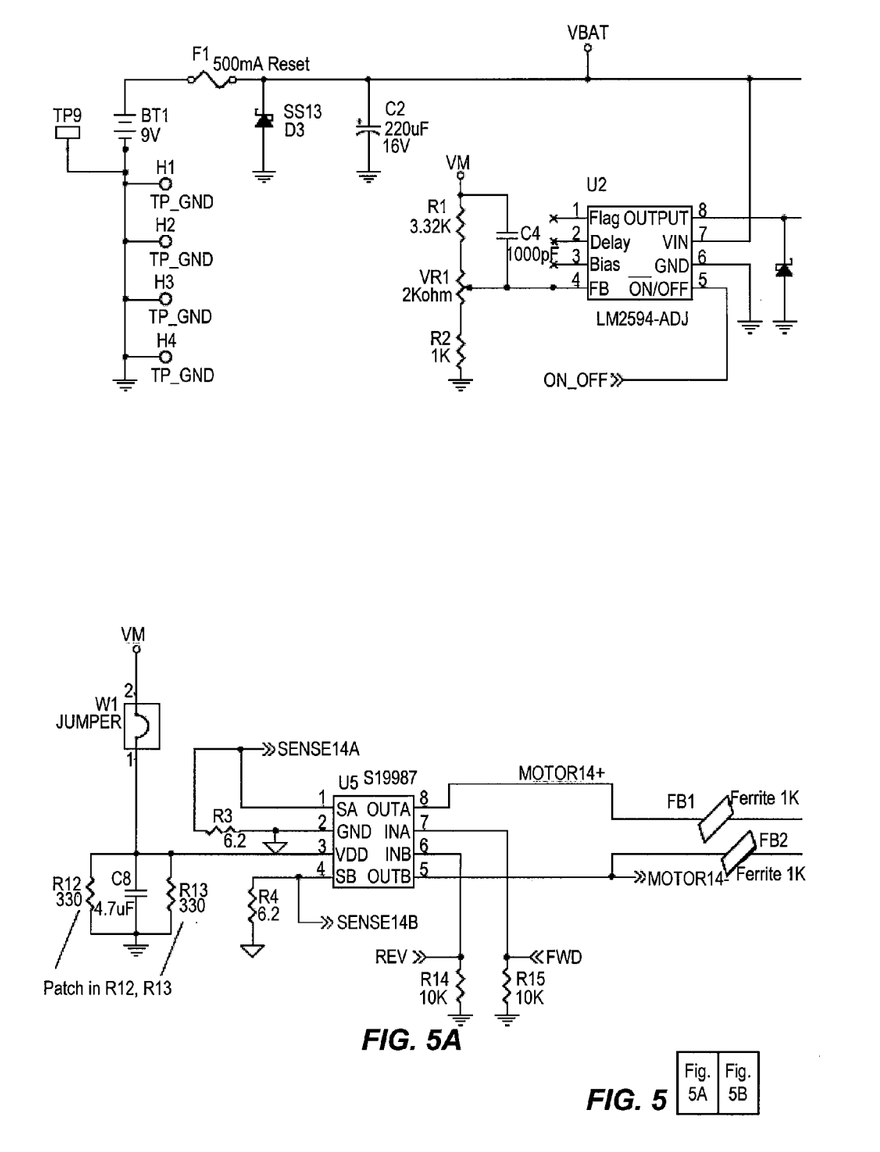
FIGS. 5 through 8 illustrate exemplary electrical schematic drawings for electronics that can be used in an embodiment of the present invention.
Figure 5B:
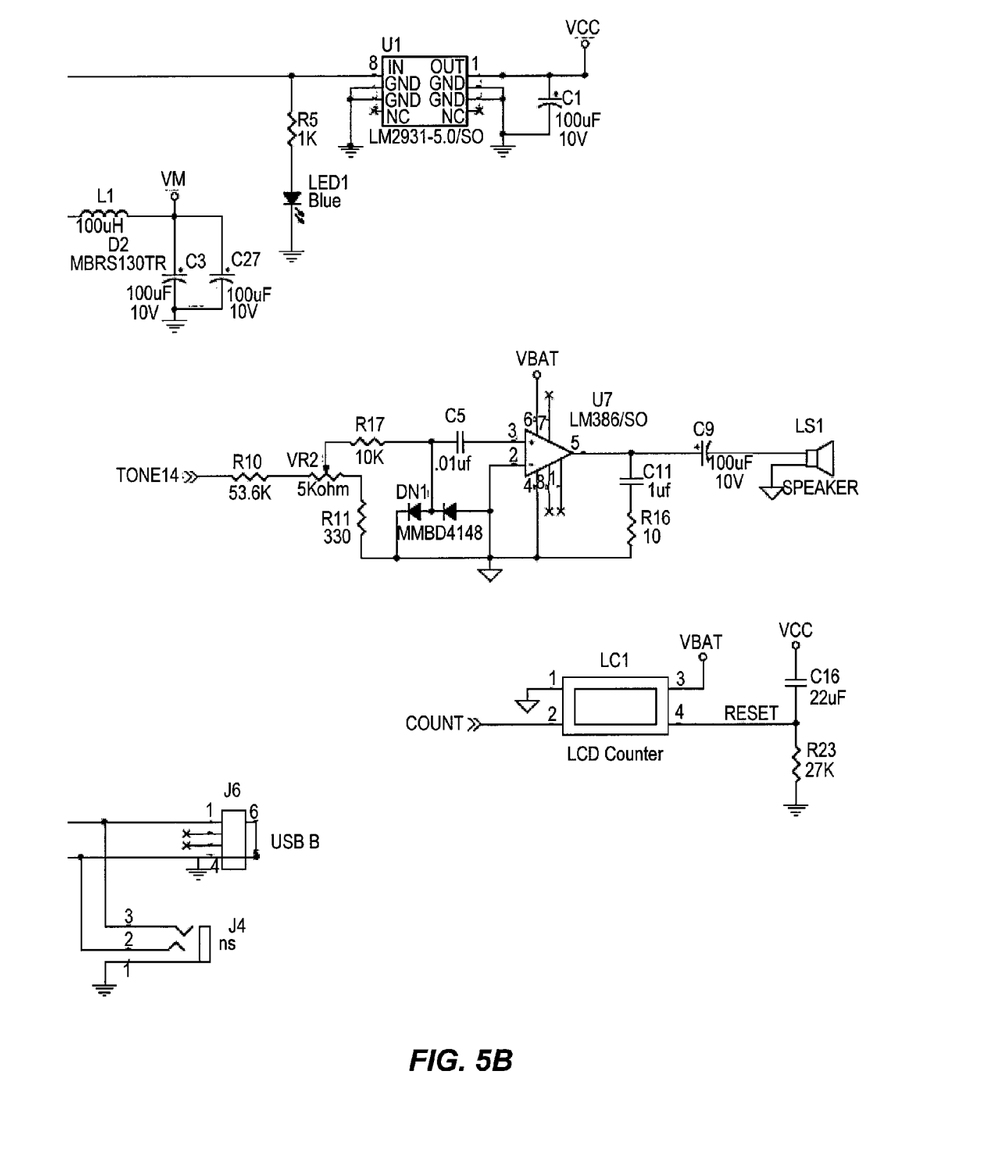
Figure 6:
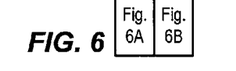
Figure 6A:
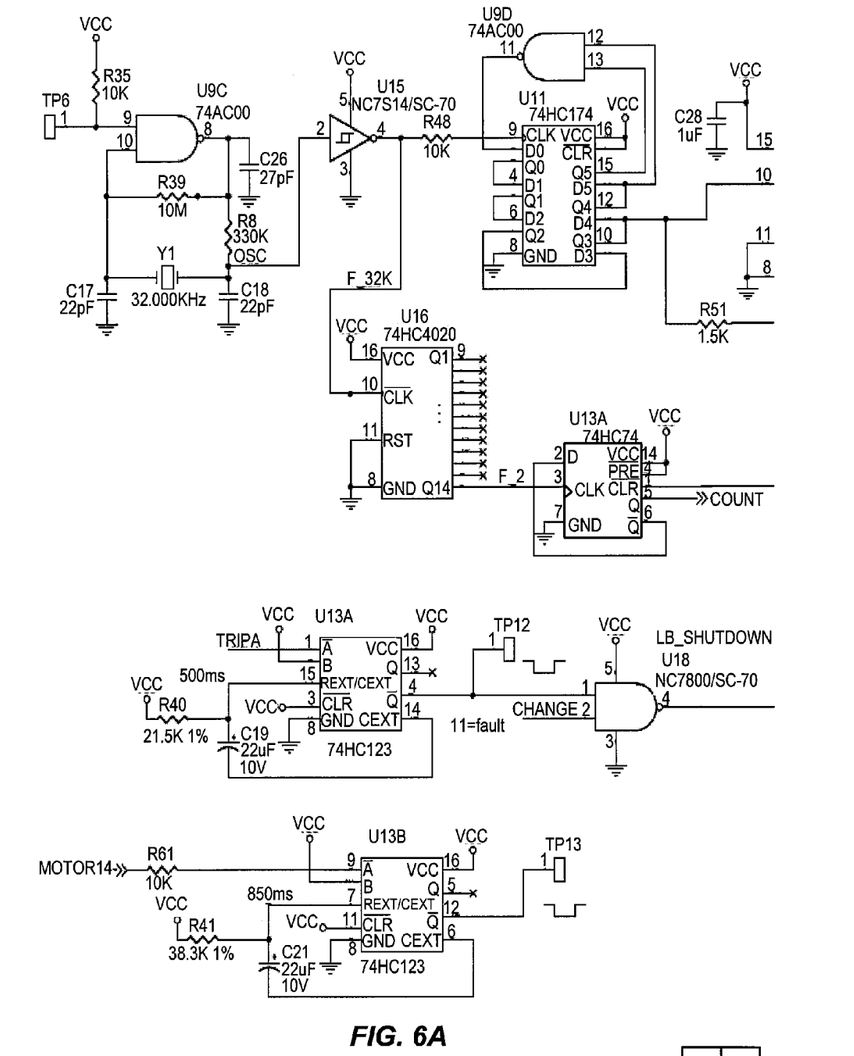
Figure 6B:
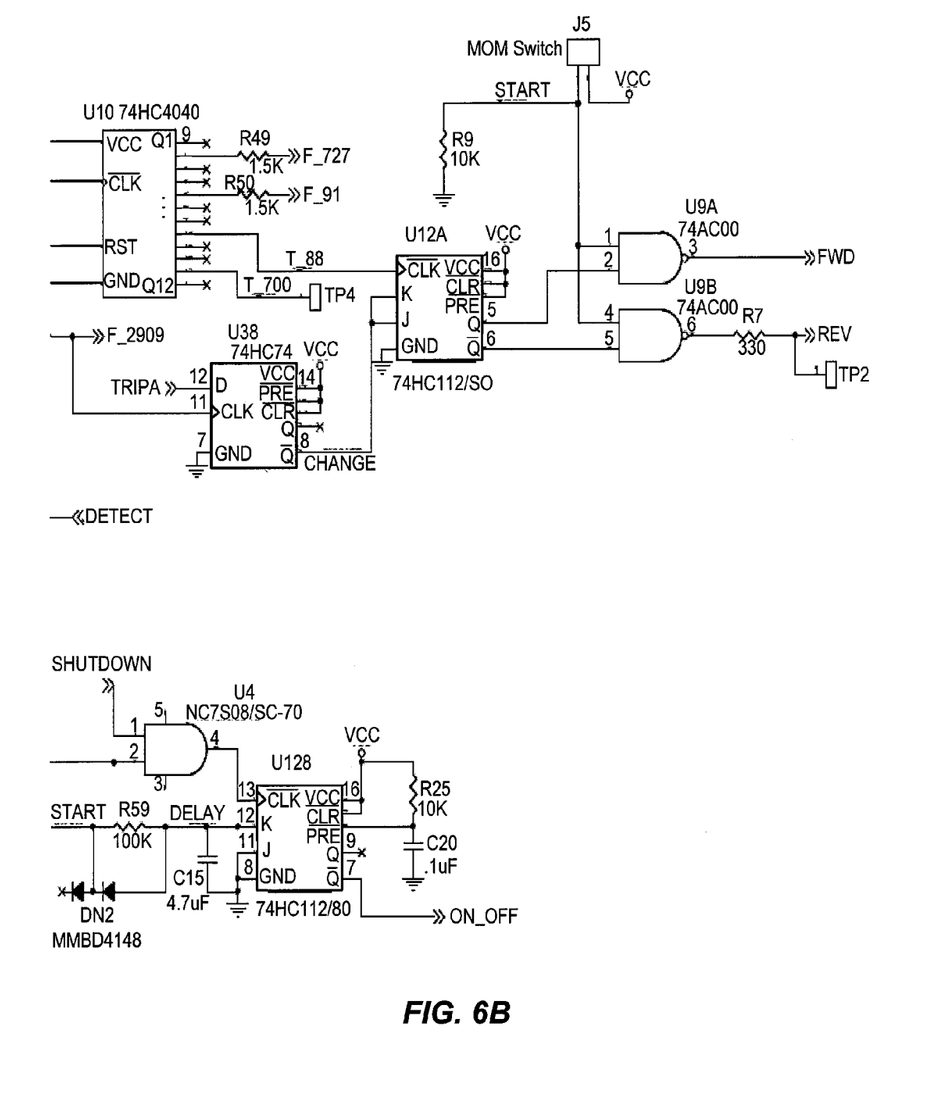
Figures 7, 7A:
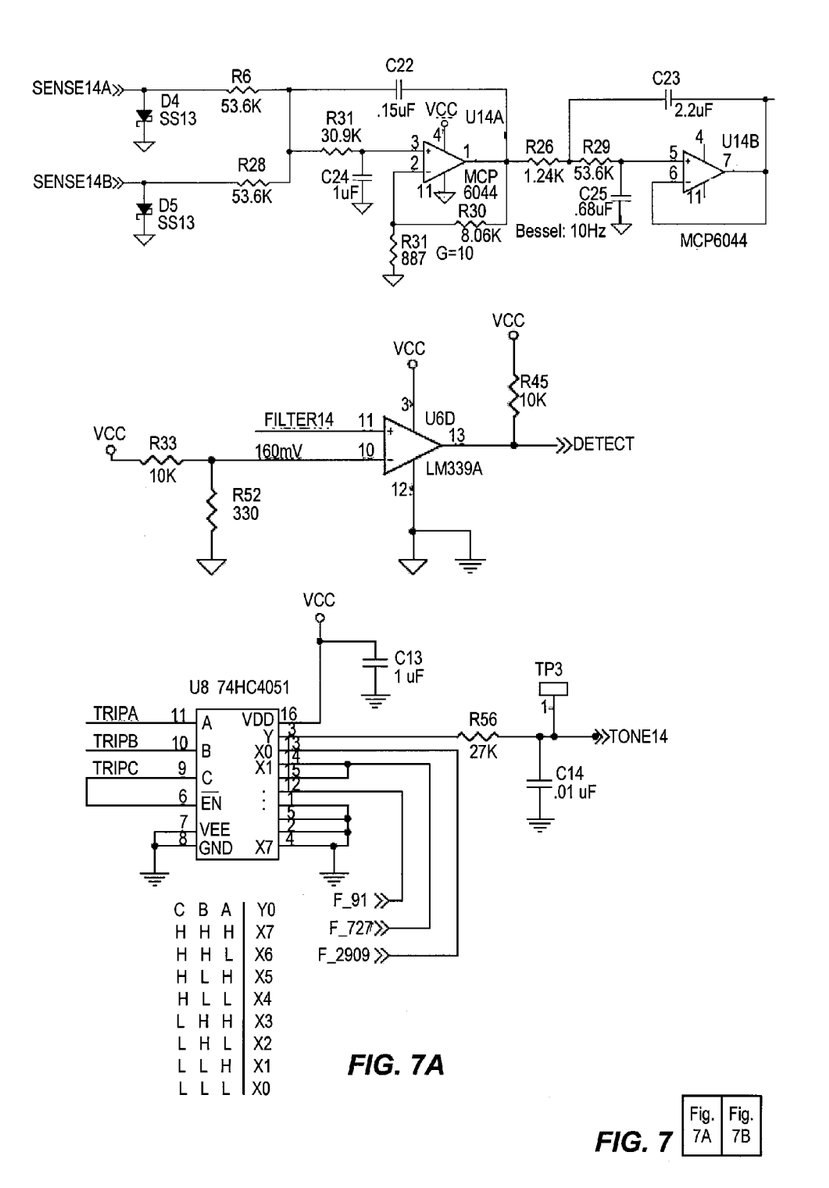
Figure 7B:
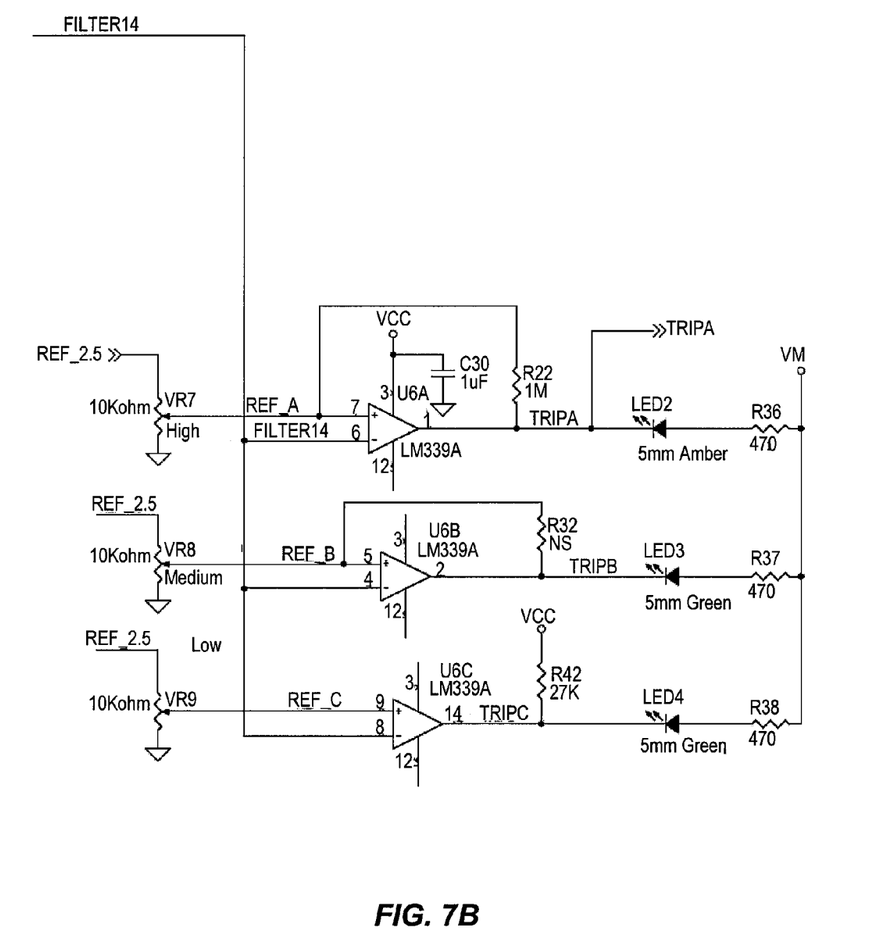
Figure 8:
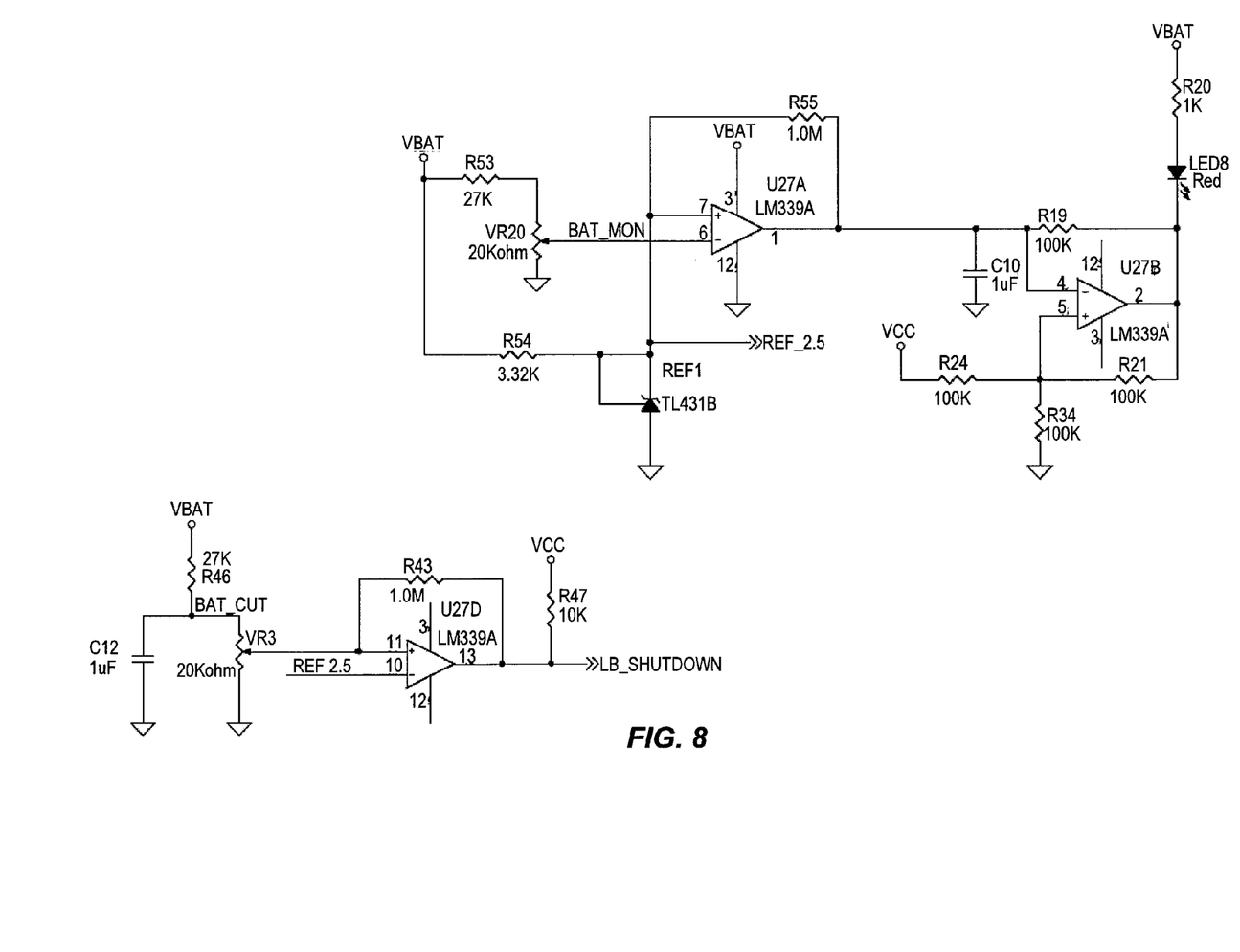

FIGS. 5 through 8 show exemplary electronic circuit diagrams of a circuitry implementation that can be used within the control unit 14 of the present invention. It is understood that many other circuit implementations, including software, firmware and/or hardware, can be used and yet still arrive at embodiments of the invention. FIG. 5 illustrates various components of the control unit 14 including the motor drive, audio components, and counter. The control unit 14 may be powered by a battery. The power supply may further include a voltage regulator which allows for adjustment of optimum motor 56 speed and torque. It will further be appreciated that the control unit 14 may alternatively be powered via voice activation, wireless activation, or Bluetooth® footswitch technology in lieu of manual activation with switch 34. FIG. 6 illustrates a sample circuit of the time base and safety shutdown. FIG. 7 illustrates s sample circuit of the voltage to frequency generator 68 and a sample circuit of the visual feedback circuitry. FIG. 8 is a sample circuit for a battery monitor.

Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. For example, it is fully contemplated that the present invention may be implemented as a separate control unit as shown in FIG. 1 or may be incorporated into a handle of the occlusion-crossing device. Therefore, the above description should not be taken as limiting the scope of the invention which is defined by the appended claims.

What is claimed is:

1. A luminal drilling system comprising:
a rotational penetrating device including an elongate member, and a drive shaft extending through said member and having a drill tip which emerges distally from a distal end of the drilling device;
a motor connectable to a proximal portion of the drive shaft to rotationally drive the drive shaft;
a load sensor coupled to the motor or to the drive shaft, wherein the sensor produces an output signal which is representative of the rotational load on the drill tip as said tip is rotated and advanced through occlusive material in a body lumen; and
motor control circuitry which reverses the direction of rotation of the motor when the sensed rotational load meets or exceeds a threshold value.

2. A luminal drilling system as in claim 1, wherein the elongate member comprises a tube having a diameter in the range from 0.008 in. to 0.04 in.

3. A luminal drilling system as in claim 2, wherein the motor may be detached from the drive shaft.

4. A luminal drilling system as in claim 2, wherein the motor includes a coupling for removably attaching the motor to the drive shaft.

5. A luminal drilling system as in claim 1, wherein the drill tip of the drilling device is adapted to penetrate equally well when rotated in either direction.

6. A luminal drilling system as in claim 1, wherein the motor is controllable to rotate at a maximum speed in the range from 5,000 rpm to 20,000 rpm.

7. A luminal drilling system as in claim 1, wherein the load sensor measures current consumption by the motor, wherein increased current consumption indicates an increase in load.

8. A luminal drilling system as in claim 1, wherein the load sensor measures rotational speed of the motor or drive shaft, wherein decreased rotational speed indicates an increase in load.

9. A luminal drilling system as in claim 1, further comprising circuitry which produces a visual and/or audible output in response to the output signal of the load sensor.

10. A luminal drilling system as in claim 9, wherein the visual and/or audible output comprises a first output level when the load is below the threshold value and a second output level when the load is at or above the threshold value to indicate that the motor direction is changing.

11. A luminal drilling system as in claim 9, wherein the visual and/or audible output comprises a first output level when there is minimal load, a second output level when there is load below the threshold value, and a third output level when load is at or above the threshold value to indicate that the motor direction is changing.

12. A rotational driver for a luminal rotational penetrating device which includes an elongate body and a drive shaft extending through said body and having a drill tip which emerges distally from a distal end of the elongate body, the driver comprising:
a motor adapted to rotational drive the drive shaft;
a load sensor coupled to the motor or to the drive shaft, wherein said sensor produces an output signal which is representative of the rotational load on the drill tip as said tip is rotated and advanced through occlusive material in a body lumen; and
motor control circuitry which reverses the direction of rotation of the motor when the sensed rotational load meets or exceeds a threshold value.

13. A rotational driver as in claim 12, wherein the motor is controllable to rotate at a maximum speed in the range from 5,000 rpm to 20,000 rpm.

14. A rotational driver as in claim 12, wherein the load sensor measures current consumption by the motor, wherein increased current consumption indicates an increase in load.

15. A rotational driver as in claim 12, wherein the load sensor measures rotational speed of the motor or drive shaft, wherein decreased rotational speed indicates an increase in load.

16. A rotational driver as in claim 12, further comprising circuitry which produces a visual and/or audible output in response to the output signal of the load sensor.

17. A rotational driver as in claim 16, wherein the visual and/or audible output comprises a first output level when the load is below the threshold value and a second output level when the load is at or above the threshold value to indicate that the motor direction is changing.

18. A rotational driver as in claim 16, wherein the visual and/or audible output comprises a first output level when there is minimal load, a second output level when there is load below the threshold, and a third output level when load is at or above the threshold value to indicate that the motor direction is changing.

* * * * *